United States Patent [19]

Friedman et al.

[11] 3,944,681

[45] Mar. 16, 1976

[54] FOODS CONTAINING SALTS OF ACETYL AMINO ACIDS AS WATER BINDERS

[75] Inventors: Herman H. Friedman, Bayside, N.Y.; Victor Moreno, Montreal, Canada

[73] Assignee: General Foods Corporation, White Plains, N.Y.

[22] Filed: Jan. 11, 1974

[21] Appl. No.: 432,723

[52] U.S. Cl. .............. 426/615; 426/641; 426/643; 426/644
[51] Int. Cl.² ........................................... A21D 4/00
[58] Field of Search ........... 426/227, 321, 335, 151, 426/212; 252/194, 384; 260/534 L, 534 E, 534 X

[56] References Cited
UNITED STATES PATENTS

| | | | |
|---|---|---|---|
| 2,857,282 | 10/1958 | Jansen | 426/321 |
| 3,290,368 | 12/1966 | Fernholz | 426/151 |
| 3,374,097 | 3/1968 | Laden | 426/162 |
| 3,782,971 | 1/1974 | van Roon | 426/212 |

FOREIGN PATENTS OR APPLICATIONS 1,086,214  8/1958  Germany ........................... 426/212

*Primary Examiner*—Norman Yudkoff
*Assistant Examiner*—Hiram H. Bernstein
*Attorney, Agent, or Firm*—Thaddius J. Carvis; Daniel J. Donovan; Bruno P. Struzzi

[57] ABSTRACT

Compounds of the general formula:

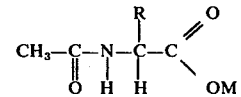

Wherein: R is a member selected from the group consisting of $-(CH_2)_n-CO_2M$, $-(CH_2)_n-NO_3$, $-(CH_2)_n-SO_3M$, and $-(CH_2)_n-NH_2$; $n$ is an integer from 1 to 4; and M is an alkali metal; are useful as water binders in a wide variety of compositions, especially food and cosmetic compositions.

10 Claims, No Drawings

FOODS CONTAINING SALTS OF ACETYL AMINO ACIDS AS WATER BINDERS

BACKGROUND OF THE INVENTION

The present invention relates to water binders, and more specifically to compositions employing a specific group of compounds having the ability to bind large amounts of water.

Water binders have a broad range of commercial signicance. There are many products, especially food and cosmetics, which will dry out upon exposure to ambient conditions. It is desirable, as suggested in U.S. Pat. No. 3,374,097 to Laden, to add a humectant to bind the water within such compositions to prevent them from drying out. Additionally, as disclosed in the copending U.S. application filed concurrently herewith in the names of Friedman, Halik and Schwarz (GF Case No. 2198), it is desirable for moisturizing cosmetic compositions to include moisturizing humectant compounds to increase the moisture level of the skin when applied thereto. Yet further, moisture binders are useful for reducing the water activity, $A_w$, in food products to make them resistant to microbial growth even when stored at ambient temperatures.

SUMMARY OF THE INVENTION

It is an object of the present invention to provide a wide range of compositions containing water bound therein.

This and other objects are accomplished according to the present invention which provides a composition comprising water, a material which tends to lose water when exposed to the atmosphere, and an amount, effective to bind water and reduce the tendency for water loss from the composition of a compound defined by the formula:

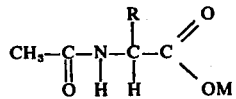

Wherein: R is a member selected from the group consisting of $-(CH_2)_n-CO_2M$, $-(CH_2)_n-NO_3$, $-(CH_2)_n-SO_3M$, and $-(CH_2)_n-NH_2$; $n$ is an integer from 1 to 4; and M is an alkali metal.

DETAILED DESCRIPTION

The present invention is based upon the discovery that compounds of the above general formula have the ability to strongly bind water within compositions. Exemplary of water binders defined by the above formula are the alkali metal salts of N-acetylated amino and imino acids. Examples of the latter series of compounds are the sodium and potassium N-acetyl-L-glutamate, the sodium and potassium salts of N-acetyl lysine, and the sodium and potassium salts of N-acetyl aspartic acid.

All of these compounds are commercially available in the acid form and can be purchased in the requisite purity for the intended use. Alternatively, they can be prepared by methods well known to the art. For example, N-acetyl-L-glutamic acid can be prepared by acetylating L-glutamic acid in aqueous solution with acetic anhydride. The resulting N-acetyl-L-glutamic acid is then purified in known manner.

Any of the alkali metal salts of these compounds which are suitable for the particular end use can be employed according to the present invention. The sodium and potassium salts are preferred. These salts can be easily prepared by neutralizing the acid form of these compounds with any suitable base containing the appropriate alkali metal cations. For example, the sodium salts of these compounds can be prepared by neutralizing the acid with a slight excess of sodium hydroxide, and the potassium salt with a slight excess of potassium hydroxide.

These salts are employed in the compositions of the present invention in any amount which is effective to bind water and reduce the tendency for water loss from the composition. Typically, these alkali metal salts will be employed in amounts greater than about 0.5% by weight of the composition. Preferably they are employed at levels of from about 1 to about 5% by weight of the composition. While the upper limit in most compositions is primarily a function of cost and a balancing of the properties of the composition with and without the addition of the water binders of the present invention, their use in food use can be limited by the levels of the alkali metals employed and the resultant salty taste of the composition. It would, of course, be possible to employ a combination of these salts in a combined amount effective to bind water and reduce the tendency of the composition to lose water.

The water binding compositions of the present invention, can have a wide range of utilities, depending upon the particular formulation of ingredients. For example, where a cosmetic preparation is desired, an emulsion comprising water and oil, with or without an emulsifier, can be admixed with one of the moisture binders of the present invention. In the cosmetic emulsion, the water binder is preferably added as the salt to the water phase; however, it may be added to the oil phase in the acid form and then neutralized in situ. When the composition of the present invention is desired to take the form of a food product, the water binder is added to an edible material. For example it may be employed in preparing intermediate moisture food products such as meat, fish, poultry, fruit and vegetable products. Exemplary of the meat products, are those for animals known as soft moist products. For example, those disclosed in U.S. Pat. Nos. 3,482,985 and 3,615,652 to H. M. Burgess et al. When added to vegetable products, the natural basic characteristic of the vegetables can aid in neutralizing the acid form of the water binding compounds to the salt form.

In food products, the water binders aid in reducing the tendency of the products to support microbial growth. In cosmetics for application to the skin, they can aid in maintaining soft, moist, healthy appearing skin. And, in all cases, they bind water and reduce the natural tendency of the compositions from drying when exposed to the atmosphere.

The following examples are presented for the purpose of further illustrating and explaining the present invention and should not be taken as limiting in any regard. Unless otherwise indicated, all parts and percentages are by weight.

EXAMPLE I

Two cosmetic preparations according to the present invention are prepared having the following formulations:

| Ingredient | Parts A | B |
| --- | --- | --- |
| glycerol monostearate | 2 | 2 |
| stearic acid | 7 | 7 |
| cetyl alcohol | 5 | 5 |
| disodium N-acetyl-L-glutamate | 3 | — |
| dipotassium N-acetyl-L-glutamate | — | 3 |
| water | 82.5 | 83 |
| perfume | 0.5 | 0.5 |

The compositions are prepared by dissolving the alkali metal N-acetyl-L-glutamate in water at about 60°C. The remaining ingredients, except for the perfume, are melted and mixed to form an oil phase. For each composition, the aqueous solution was added to the oil phase and stirred to form a uniform mass while cooling. The perfume is added last. The resultant mixture is useful as a moisturizer.

EXAMPLE II

The following is a formulation of an intermediate moisture pet food product containing meat meal:

| | |
| --- | --- |
| Water | 24.1 |
| Meat meal | 11.3 |
| Soy flakes | 35.5 |
| Sucrose | 13.0 |
| Soya hulls | 8.1 |
| Sorbitol | 2.1 |
| Tallow | 4.2 |
| Sodium chloride | 1.0 |
| Potassium sorbate | 0.3 |
| Propylene glycol | 2.1 |
| Garlic | 0.2 |
| Red dye | 0.01 |
| Disodium N-acetyl-L-glutamate | 2.0 |

EXAMPLE III

Fresh carrots are infused by a stabilizing solution at just below boiling for a period of about 18 hours. The carrots are peeled and trimmed before treatment in the following stabilizing solution:

| Ingredient | % |
| --- | --- |
| Glycerol | 85.0 |
| Water | 5.5 |
| Sodium Chloride | 3.7 |
| Disodium N-acetyl-L-glutamate | 5.3 |
| Potassium sorbate | 0.5 |
| | 100 |

The carrots thus treated are more stable against microbial attack. Other vegetables are treated in similar manner.

Many modifications and variations of the present invention will be apparent to those skilled in the art upon reading the above disclosure. It is intended that all such modifications and variations be included within the scope of the present invention as defined by the following claims.

What is claimed is:

1. A food product comprising: (a) a material selected from the group consisting of meat, fish, poultry, fruits and vegetables, which tends to lose water when exposed to the atmosphere; and (b) an amount, effective to bind water and reduce the tendency for water loss from the composition, of a water binding compound defined by the formula

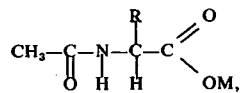

Wherein: R is a member selected from the group consisting of $-(CH_2)_n-CO_2M$, $-(CH_2)_n-NO_3$, $-(CH_2)_n-SO_3M$, and $-(CH_2)_n-NH_2$; $n$ is an integer from 1 to 4; and M is an alkali metal.

2. A composition according to claim 1 wherein M is potassium.

3. A composition according to claim 1 wherein M is sodium.

4. A composition according to claim 3 wherein R is $-(CH_2)_4-NH_2$.

5. A composition according to claim 1 wherein R is $-(CH_2)_4-NH_2$.

6. A composition according to claim 1 wherein R is $-(CH_2)-CO_2M$.

7. A composition according to claim 1 wherein R is $-(CH_2)_2-CO_2M$.

8. A composition according to claim 7 for use as a food product, wherein the material which would tend to lose water is a vegetable.

9. A composition according to claim 7 for use as a food product, wherein the material which would tend to lose water is a meat product.

10. A composition according to claim 9 wherein M is sodium and the water binding compound is employed at a level of from about 1 to about 5%.

* * * * *